United States Patent [19]

Mason et al.

[11] Patent Number: 4,768,500
[45] Date of Patent: Sep. 6, 1988

[54] KNEE PROTECTOR

[75] Inventors: Bradley R. Mason, Carlsbad; Jeffrey T. Mason, Escondido, both of Calif.

[73] Assignee: Don Joy, Inc., Carlsbad, Calif.

[21] Appl. No.: 13,236

[22] Filed: Feb. 10, 1987

Related U.S. Application Data

[63] Continuation-in-part of Ser. No. 756,660, Jul. 29, 1985, Pat. No. 4,643,176, which is a continuation-in-part of Ser. No. 657,356, Oct. 3, 1984, abandoned.

[51] Int. Cl.⁴ ................................................ A61F 3/00
[52] U.S. Cl. ..................................... 128/80 C; 128/88
[58] Field of Search ................. 128/80 C, 80 F, 80 A, 128/80 B, 80 R, 80 E, 80 H, 87 R, 88

[56] References Cited

U.S. PATENT DOCUMENTS

| | | | |
|---|---|---|---|
| 2,587,166 | 2/1952 | Jovick | 128/80 C |
| 3,587,572 | 6/1971 | Evans | 128/80 C |
| 4,144,592 | 3/1979 | Larson | 128/80 C |
| 4,183,099 | 1/1980 | Lacey | 128/80 C |
| 4,312,335 | 1/1982 | Daniell, Jr. | 128/80 C |
| 4,487,200 | 12/1984 | Feanny et al. | 128/80 C |
| 4,617,920 | 10/1986 | Carsalade | 128/80 F |
| 4,643,176 | 2/1987 | Mason et al. | 128/80 C |

Primary Examiner—Edgar S. Burr
Assistant Examiner—Huong Q. Pham
Attorney, Agent, or Firm—Albert L. Gabriel

[57] ABSTRACT

An athletic knee protector is disclosed wherein a bowed leaf spring hinge structure is supported on load distribution pads or cuffs attached to the thigh and shin of the wearer and is spaced laterally from the lateral side of the knee to protect the knee of an athlete against injury from lateral forces and impacts such as are likely to occur in football. The bowed leaf spring hinge structure absorbs such forces and impacts and redistributes them at locations spaced substantially above and below the knee proximate the strong bones of the leg. Preloading of knee ligaments in the lateral/medial direction is avoided, and lateral forces and impacts are better distributed, by connecting the pads or cuffs to the hinge structure with a free rocking or pivoting action in the lateral/medial direction. Also, the pads or cuffs are made more adaptable to the curvature of the leg by a variable flexibility in the anterior/posterior direction so that attachment and working loads applied to the leg are spread out more uniformly.

15 Claims, 5 Drawing Sheets

KNEE PROTECTOR

RELATED APPLICATIONS

This is a continuation-in-part of our co-pending application Ser. No. 06/756,660 filed July 29, 1985 now patented: 4,643,176 for ATHLETIC KNEE PROTECTOR, which in turn was a continuation-in-part of our application Ser. No. 06/657,356 abandoned 12/21/1985 filed Oct. 3, 1984 for ATHLETIC KNEE PROTECTOR.

BACKGROUND OF THE INVENTION

1. Field of the Invention

The present invention relates to orthopedic devices for protecting the human knee, and it relates more particularly to an orthopedic device adapted to protect the knee against injury from lateral forces and impacts which may occur during sports activities.

2. Description of the Prior Art

There is widespread need for knee protection apparatus capable of absorbing forces or impacts directed toward the lateral side of the knee and redistributing such forces or impacts along the leg so as to protect a previously injured knee from further injury. A typical circumstance where such knee protection equipment would be desirable is during a game of football, where for example the person with a previously injured leg has that leg planted and another player puts a shoulder pad into the lateral side of the leg.

Applicants are aware of only two prior art protective devices directed to this specific problem, and neither of these devices has proven sufficiently satisfactory to come into widespread use. These two prior art devices are made in accordance with disclosures in U.S. Pat. No. 4,249,524 to Anderson and U.S. Pat. No. 3,528,412 to McDavid. The Anderson device consists of arms adapted to be attached to the lateral side of the thigh and calf, respectively, either by tape or neoprene wrap held with Velcro. The proximal or near ends of the arms (relative to the knee) are pivotally connected to opposite ends of a rigid metal bridge, the purpose of the device being to receive lateral forces at the bridge instead of such forces being applied directly to the knee, and to distribute such lateral forces to the femur and tibia. The Anderson device is intended to be used by football players, but it has problems such that football players in fast running positions, such as running backs, ends and the like, will not wear it. One problem is that the Anderson device has single-overlap pivots which must be fairly tight for stability, resulting in too much friction during running and hence impairment of full running freedom. Another problem with the Anderson device is that lateral force against the bridge tends to be applied to the leg primarily directly under the regions of the pivots, which is still fairly well localized at regions close to the knee, and not distributed well along the lengths of the arms to which the bridge is pivoted. A further problem with the Anderson device is that although it is biaxially pivotal, the movements at the two pivots are completely independent of each other, so that just one or just the other of the pivotal connections may move, which may cause slippage. Also, the pivots are too far apart to simulate the hinging action of the human knee.

The device of the McDavid patent is essentially the same as the Anderson device except it has only a single single-overlap pivot located generally proximate the knee. The McDavid device has the same two principal problems as the Anderson device, namely, the single-overlap pivot needs to be fairly tight for stability, resulting in an undesirably large amount of friction during running, and lateral forces against the raised pivot tend to be applied to the leg at localized regions close to the knee and not distributed well along the lengths of the pivoted arms strapped to the thigh and calf.

A further problem with both the Anderson and McDavid prior art athletic knee protective devices is that they cause lateral forces and impacts to be applied so close to the knee as to be applied substantially directly to bone, namely to the femur and fibia proximal the knee. This causes further localization of force and impact application, with the further likelihood of trauma directly to the femur and the immediate covering tissues.

Applicants are aware of a number of other prior patents directed to knee braces for protecting or supporting or limiting the motion of injured knees, but are not aware of any devices other than the Anderson and McDavid devices manufactured for the purpose of protecting the knee from lateral forces or impacts. Two of these other patents, Erichsen U.S. Pat. No. 4,381,768 and Lerman U.S. Pat. No. 4,372,298 are relevant to the present invention because of biaxial, geared hinge structures similar to the geared hinge structure employed in applicants' invention. Stops are provided on the Lerman gears to limit the travel in both directions. However, neither the Erichsen or Lerman devices would be usable to absorb and redistribute lateral forces or impacts. Thus, in both of these patents, the hinged arms are described as being rigid. In Erichsen, the hinge appears to be right against the side of the knee so that lateral forces or impacts would be directly transmitted to the knee, and in Lerman, pads are attached to the hinges of opposite sides of the knee, so that lateral forces or impacts against the hinge on the lateral side of the knee would be transmitted through the respective pad directly to the knee.

Cummins U.S. Pat. No. 4,245,629 states that one of the purposes of the disclosed device is for absorbing and spreading an external blow, and Cummins is also of interest because it discloses a biaxial-type hinge structure, although it is not geared. This is a double overlap-type hinge with three tongues, described as being rigid, extending from each side of the hinge and independently pivoted in the hinge. The Cummins device does not appear to space the hinge structure from the knee, and it appears that lateral forces or impacts against the hinge would be applied directly to the knee joint or through the rigid tongues to localized regions of the leg very close to the knee.

McClure, Jr. U.S. Pat. No. 3,350,719 discloses substantially flat upper and lower brace bars that appear to be rigid, connected at a biaxial hinge. Lateral forces or impacts would either be applied through the hinge directly to the knee or through the brace bars to localized regions close to the knee.

Peckham U.S. Pat. No. 3,194,233 discloses lateral and medial leaf-type springs whch bow outwardly. There is no means disclosed in this Peckham patent for spreading force to the femur awd tibia at substantial spacings from the knee, and sponge pads are compressed against opposite sides of the knee joint by knee-encircling members which would cause impacts to be transmitted directly proximate the knee joint. Another Peckham U.S. Pat.

No. 2,467,907 also discloses bowed springs, but so arranged that impacts would be applied directly to the knee joint. Schulman U.S. Pat. No. 3,074,400 also discloses springs in a kneecap brace, but these are not hingedly connected. Patents such as Whitehead U.S. Pat. No. 3,898,697 and Buring 4,409,689 are exemplary of a number of patents which disclose shell-like forms fitting over portions of the upper and lower leg adjacent to the knee.

Another problem which particularly adversely affects the performance of the prior art athletic knee protective devices disclosed in the Anderson U.S. Pat. No. 4,249,524 and the McDavid U.S. Pat. No. 3,528,412, and which also adversely affects the performance of other knee braces in general, is that such devices tend to preload the knee with an unnatural force couple which predisposes the knee to injury. Such preloading is compounded in athletic knee protective devices such as those of Anderson and McDavid by variations in the preloading which occur during athletic movements, and also by the intensification of lateral forces and impacts to the protective devices.

This preloading phenomenon occurs in the following way. The knee braces have a thigh bar which is hingedly connected to a shin bar by hinge means which is pivotal in the anterior/posterior direction, but which is substantially rigid in the lateral/medial direction. The thigh and shin bars are either directly strapped or taped to the thigh and shin, respectively, as with the Anderson ad McDavid devices, or are attached to the thigh and shin through some sort of cuff or pad devices which are in turn strapped or taped to the thigh and shin. There are wide variations in the longitudinal contours of the outer or lateral side of the human leg, and as a general rule, the brace bars, cuffs or the like do not accurately align with the external lateral contours of the legs to which they are applied, and when the attachment is secured by strapping or taping, then this misalignment will result in a lateral/medial type of preloading at the knee. The relative geometry between the contours of the thigh and shin will vary for various angles of flexion of the knee, and for varying conditions of muscle flexure of the thigh and shin muscles, so that this preloading will vary during activity of the wearer, and of course this becomes most intense for the heavy athletic endeavors for which athletic knee protectors such as the Anderson and McDavid protectors are designed. With regard to the Anderson and McDavid prior art athletic knee protective devices, this problem is further compounded by two factors. The first is that the single overlap-type pivots employed in the Anderson and McDavid devices are, as aforesaid, required to be fairly tight for stability, which means that there is little or no lateral give at the pivots to compensate for the preloading. The second factor is that the Anderson and McDavid devices are intended to protect the knee against lateral forces and impacts, and with the knee in a preloaded condition, such lateral forces and impacts are more likely to cause injury to the knee than if the knee were not preloaded.

Prior to the present invention, the only known means for reducing the adverse effects of preloading was the use of braces custom-made to fit the lateral contours of invdividual legs. However, this was tedious and expensive, and did not accommodate the variations in leg contour associated with movement.

Another problem which is, again, most serious with respect to knee braces specifically intended for protection against lateral forces and impacts such as the Anderson and McDavid braces, but which is also a problem with other knee braces in general, is that the anterior/posterior contours of the braces where they are attached to the thigh and shin do not, in general, match the corresponding anterior/posterior curvatures of the thighs and shins of the wearers. This tends to concentrate the attachment and operational loads of the braces at localized regions of the thigh and shin, which can cause discomfort to the wearer and instability of the brace in operation. This problem is most severe in knee protective devices such as those of Anderson and McDavid where the rigid brace bars themselves are directly strapped or taped to the thigh and shin, and where they are intended to transmit lateral forces and impacts to the thigh and shin.

SUMMARY OF THE INVENTION

In view of these and other problems in the art, it is a general object of the present invention to provide an athletic knee protector capable of receiving and absorbing lateral forces and impacts that otherwise would be applied to the lateral side of a knee, and redistributing such forces and impacts at locations spaced substantially from the knee and in regions of strong bones of the leg.

Another general object of the invention is to provide an athletic knee protector capable of receiving and absorbing lateral forces and impacts that otherwise would be applied directly to the knee, and redistributing such forces and impacts at regions of the leg spaced substantially from the knee in such a way that the forces and impacts are, in effect, distributed generally over the whole leg as opposed to just on the point of the blow or closely adjacent to the knee.

Another object of the invention is to provide an athletic knee protector which utilizes a novel bowed leaf spring hinge structure connected at its ends to generally rigid thigh and shin pads, the bowed leaf spring hinge structure being capable of absorbing forces and impacts directed toward the lateral side of the knee and distributing such forces and impacts in a cushioned manner through the pads to the thigh and shin at locations remote from the actual knee joint.

It is another object of the invention to provide a bowed leaf spring athletic knee protector capable of receiving shocks or impacts and spreading these out at locations on the leg remote from the knee joint, and also spreading out the time of application of such blows or impacts so as to greatly reduce the shock characteristics thereof.

A further object of the invention is to provide an athletic knee protector embodying a bowed leaf spring hinge structure covered by a foam elastomer sleeve or sheath which protects from injury another person who may impact the spring-like structure, and also cooperates with the leaf spring structure in extending the time of application of any impact to the wearer of the device.

A still further object of the invention is to provide an athletic knee protector of the character described which embodies a biaxial, geared hinge that closely follows the hinge action of the human knee and has minimal frictional resistance to its hinging action, whereby full, free running movement is achievable by an athlete wearing the device, so that athletes such as football running backs are able to wear the device without their movements being materially impeded.

Another general object of the invention is to provide, particularly in an athletic knee protector but also in knee braces in general, means for preventing preloading of the knee both statically and dynamically during flexion of the knee, thereby avoiding the usual predisposition of the knee to injury from preloading when athletic knee protectors or braces are worn.

Another related general object of the invention is to provide means for preventing preloading of the knee by an athletic knee protector or knee brace without the need for the knee protector or brace being custom made to fit the contours of individual legs.

A further related object of the invention is to provide, particularly in an athletic knee protector but also in knee braces in general, load distribution pads or cuffs which are pivotally connected to the respective hinged leaf spring members or brace bars so as to be rockable or tiltable in the general lateral/medial direction, which allows the load distribution pads or cuffs to self-adjust to the lateral or outer contours of the leg so as to substantially completely eliminate any tendency for the knee protector or brace to preload ligaments of the knee at any condition of flexion of the knee, or during working of the knee as during walking or running.

A further object of the invention is to provide an athletic knee protector of the character described in which a floating or rocking action of the load distribution pads or cuffs relative to the leaf spring structure causes lateral loads and impacts to be more uniformly distributed over the areas of the load distribution pads or cuffs as the forces and impacts are applied to the leg.

A further object of the invention is to provide, particularly in an athletic knee protector of the character described, but also in knee braces in general, cuffs or load distribution pads which connect the leaf spring members or brace bars to the thigh and shin which have a variable rigidity in the anterior/posterior direction from generally rigid centrally where they connect to the leaf spring members or brace bars to somewhat flexible anterior/posterior portions, for improved adaptation of the cuffs or pads to the curvature of the leg; and when coupled with a concavity of the cuffs or pads which has a somewhat smaller cylindrical radius of curvature than the curvatures of the lateral side of the leg against which the cuffs or pads are secured, the sides of the cuffs or pads will flex outwardly in their attached positions against the leg, thereby attaching more securely to the leg and distributing lateral forces and impacts more uniformly over the areas of the cuffs or load distribution pads.

Yet another object of the invention is to provide, particularly in an athletic knee protector of the character described, but also in knee braces in general, cuffs or load distribution pads which have both a rocking action and a variable rigidity which combine to generally uniformly spread the leg engagement loads of the cuffs or pads over their entire areas, including both attachment loads and the loads of lateral forces and impacts in the case of the athletic knee protector of the invention.

The athletic knee protector of the present invention comprises a pair of leaf springs, preferably made of aluminum for lightness in weight, one of which is an upper leaf spring connected to a thigh load distribution pad or cuff, and the other of which is a lower leaf spring connected to a shin pad or cuff. The other ends of the two leaf springs are pivotally connected between a pair of spaced hinge plates, also preferably of aluminum, in a double-overlap or sandwich hinge construction, with the ends of theleaf springs having arcuate arrays of meshed gear teeth theron which cause the leaf springs to pivot cooperatively in such a way as to closely resemble the hinge action of the knee.

The leaf springs are long and are attached to the load distribution pads or cuffs at regions spaced a considerable distance above and below the knee so that lateral stresses or impacts applied to the actual hinge proximate the knee are distributed along the leg at substantial distances from the knee. The springs bow outwardly to place the majority of the lengths of the springs as well as the actual hinge at a substantial spacing from the knee, and there is no intervening material between the hinge and the knee that could contact the knee so that substantially all of the impacting or other lateral force is spread out at locations a considerable distance from the knee, and the leaf springs are free to flex under the stresses of impacts and thereby soften the blows as they are applied to the regions remote from the knee. Impacts are further softened by being applied through the load distribution pads or cuffs to large muscle masses of the thigh and shin which are remote from the bony structures of the leg near the knee.

The double-overlap or sandwich-type hinge construction has sufficient lateral stability to enable the pivoted end portions of the leaf springs to be freely pivoted between the hinge plates while at the same time the hinge is enabled to effectively rigidly connect the pivoted ends of the two springs relative to each other in the lateral direction, so that the overall bowed leaf spring structure including the hinge acts effectively as a single long bow-shaped spring at its various hinged positions. A pair of positive stop shoulders on the hinged ends of the leaf springs lock the springs against further movement at a slightly extended position of the knee so as to prevent hyperextension.

Foam elastomer linings are provided on the inner surfaces of the load distribution pads or cuffs to cushion the engagment between the pads and the skin. Wrap-around elastomer attachment sheets are attachable by Velcro to the outer surfaces of the pads and are adapted to be stretched around the thigh and calf and their respective pads and secured to themselves by Velcro. A foam elastomer sleeve or sheath is placed over the hinge and the bowed portions of the leaf springs to protect from injury another person who might impact against these structures, and this also serves to cooperate with the leaf springs in softening the application of impacts to the leg.

In a presently preferred embodiment of the invention, each of the load distribution pads or cuffs is mounted on its respective leaf spring member to have a floating or rocking action relative to the leaf spring member. The load distribution pad or cuff rocks about a fulcrum, with the rocking axis transverse to the longitudinal direction of the respective leaf spring member and directed in the general anterior/posterior direction so that the rocking movement is in the general lateral/medial direction. This rocking action allows the load distribution pads or cuffs to self-adjust to the lateral or outer contours of the leg so as to substantially completely eliminate any tendency for the athletic knee protector to preload ligaments of the knee at any condition of flexion of the knee, or during working of the knee as in walking or running. This floating or rocking action also helps assure substantially uniform distribution of lateral forces and impacts over the areas of the load distribution pads or cuffs as the forces and impacts are applied to the leg.

In this presently preferred embodiment of the invention, the load distribution pads or cuffs have a variable flexibility in the anterior/posterior direction, varying from generally rigid centrally where the pad or cuff is attached to the leaf spring member to somewhat flexible anterior/posterior portions, for improved adaptation of the pads or cuffs to the curvature of the leg. This variable flexibility may be coupled with a concavity of the pads or cuffs which is somewhat smaller or tighter than the curvature of the outer or lateral side of the leg against which the pad or cuff is secured. Thus, the anterior/posterior side portions of the pads or cuffs flex laterally outwardly in their attached positions against the leg for better attachment, and the pads or cuffs distribute lateral forces and impacts more uniformly over the entire areas of the pads or cuffs.

The rocking action and variable flexibility of the load distribution pads or cuffs in the presently preferred form of the invention have particular utility in the athletic knee protector of the invention because they enable lateral forces and impacts to be generally uniformly applied to the leg over the entire areas of the pads or cuffs, avoiding localization in the application of such stresses. Also, the avoidance of preloading by the rocking action of the pads or cuffs is particularly important in the athletic knee protector of the invention because preloading is most likely to cause damage under the high level of activity associated with athletic endeavor. Nevertheless, both the rocking action and the variable flexibility of the pads or cuffs are useful improvements for knee braces in general because of the avoidance of preloading and spreading of attachment and working loads more uniformly over the areas of the pads or cuffs.

BRIEF DESCRIPTION OF THE DRAWINGS

These and other objects of the invention will become more apparent in view of the following description taken in conjunction with the drawings, wherein.

DETAILED DESCRIPTION

A first form of athletic knee protector according to the invention, generally designated 10, is illustrated in FIGS. 1-8 of the drawings. Athletic knee protector 10 is adapted to be attached to the thigh and shin of the user in the manner shown in FIGS. 6, 7 and 8 to present a bowed leaf spring hinge structure generally designated 12 in spaced relationship to the lateral or outer side of the knee to protect the knee of an athlete against injury from lateral forces and impacts such as are likely to occur in football and soccer. The knee protector 10 of the invention also provides support for a previously injured knee. Despite such protection and support afforded by the athletic knee protector 10 of the invention, its unique leaf spring hinge structure 12 enables full, free running movement to be achieved by an athlete wearing the device, so that athletes such as football running backs who heretofore would not wear devices of this general type find the present invention does not impede their movements, and are accordingly willing to wear the athletic knee protector 10 of the invention.

The knee protector 10 as illustrated in the drawings is arranged to protect the right knee. The same knee protector 10 is used inverted for the left knee so that its parts are reversed or arranged as a mirror image relative to those of the knee protector 10 as shown in the drawings.

Figure 1:
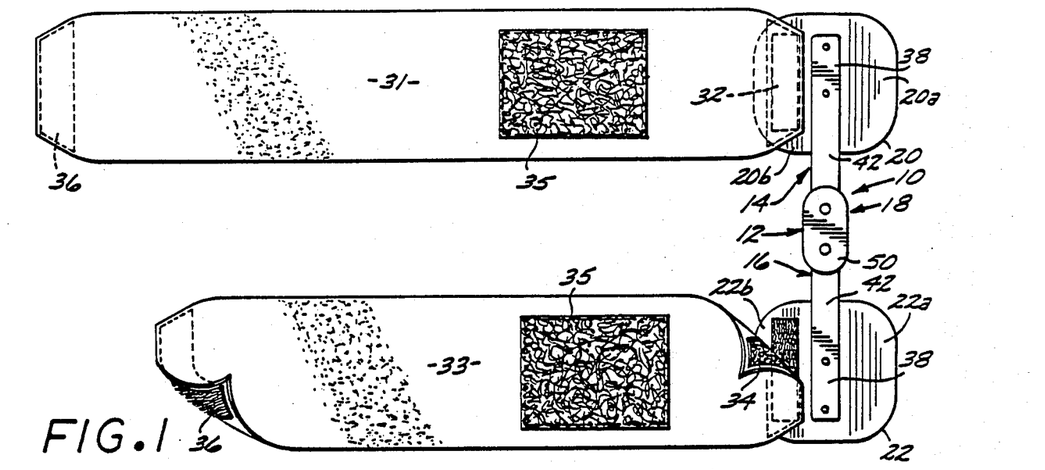
FIG. 1 is a plan view of a fully assembled first form of athletic knee protector according to the invention, laid out generally flat with the outer serfaces of the device facing upwardly.

The overall construction of the athletic knee protector 10 of the invention is best seen in FIG. 1, wherein the fully assembled device is laid out generally flat with the outer surfaces of the device facing upwardly. The leaf spring hinge structure 12 consists of upper and lower leaf spring members 14 and 16 hingedly connected by means of a biaxial or bicentric hinge 18. The leaf spring hinge structure 12 will be described hereinafter in detail in connection with FIGS. 2-4 of the drawings, and is essentially the same for all three forms of the invention shown and described hereinafter. An upper end portion of the upper leaf spring member 14 is attached to an upper portion of a thigh load distribution pad 20, and similarly, a lower end portion of the lower leaf spring member 16 is attached to a lower portion of a shin load distribution pad 22. In the forms of the invention shown in FIGS. 1-8 and FIGS. 9-12, these attachments of the leaf spring members to the load distribution pads are rigid, while in the form of the invention shown in FIGS. 13-21, the attachments of the spring members to the load distribution pads are such as to allow a rocking action of the load distribution pads relative to their respective leaf spring members for self-adjustment of the pads to the lateral or outer contour of the leg of the wearer.

The load distribution pads 20 and 22 are made of substantially rigid sheet plastic material such as a high density polyethylene which has sufficient rigidity or stiffness when operatively mounted on the leg to distribute a load or impact over a considerable area of the leg. The load distribution pads 20 and 22 are contoured so as to substantially conform with average configurations of the lateral side of the thigh and shin when operatively mounted on the leg. Referring to FIG. 1, each of the load distribution pads 20 and 22 has a respective anterior portion 20a and 22a and posterior portion 20b and 22b.

Foam elastomer linings 28 and 30, which are at least coextensive with the pads 20 and 22 and which may be made of foam neoprene, are bonded to the inner surfaces of the respective thigh and shin pads 20 and 22 to serve the multiple functions of providing soft cushioning under the generally hard pads and providing anti-slip engagement with the skin. An elongated elastomer attachment sheet 31, which may or may not be foam elastomer, is releasably attachable to the outer surface of the posterior portion 20b of pad 20 by Velcro means 32 and extends posteriorly of such attachment; and a similar, somewhat shorter elastomer attachment sheet 33 is releasably attachable to the outer surface of the posterior portion 22b of pad 22 by Velcro means 34 and extends posteriorly of such attachment.

An outwardly facing Velcro pad 35 is mounted on each of the elastomer sheets 31 and 33 adjacent to the respective pads 20 and 22, and a complementary inwardly facing Velcro hook strip 36 is mounted on each of the elastomer sheets 31 and 33 proximate its free end.

The athletic knee protector 10 is mounted on the leg by placing the foam linings 28 and 30 of respective load distribution pads 20 and 22 against the lateral sides of the thigh and shin, respectively, then wrapping the attachment sheets 31 and 33 posteriorly around the thigh and calf, respectively, and then anteriorly medially and then over the exposed surfaces of the respective load distribution pads 20 and 22 and the attached end portions of the respective leaf spring members 14 and 16, and then attaching the Velcro strips 36 to the respective Velcro pads 35. This wrap-around attachment is made sufficiently tightly to stretch the elastomer attachment wraps 31 and 33 so as to firmly secure the cushioned pads 20 and 22 to the thigh and shin, respectively. In this operative, mounted location of the athletic knee protector 10, the foam elastomer linings 28 and 30 underlying the respective pads 20 and 22 not only protect skin and flesh from the generally rigid shells, but also provide an anti-slip engagement with the skin which gives some control against downward migration of the knee protector 10.

An alternative means for mounting the pads 20 and 22 on the thigh and shin, respectively, is to tape each of the pads 20 and 22 into position. If this is to be the case, the attachment wraps 31 and 33 would be removed from the knee protector 10 by disengagement of the respective Velcro means 32 and 34.

Figure 2:
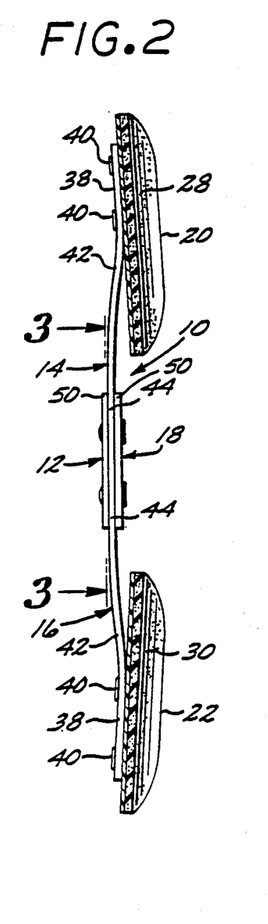
FIG. 2 is a vertical section taken on the line 2—2 of FIG. 1.
Figure 3:
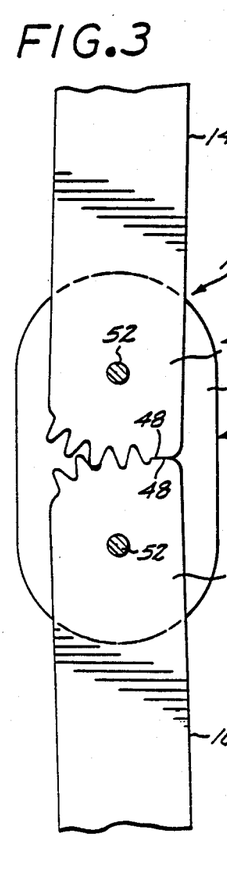
FIG. 3 is a sectional view, partly in elevation, taken on the line 3—3 in FIG. 2 greatly enlarged from FIGS. 1 and 2, but with the parts shown in approximately the same size as an actual device made in accordance with the invention, the leaf spring hinges being fully extended to the stop position in FIG. 3.
Figure 4:
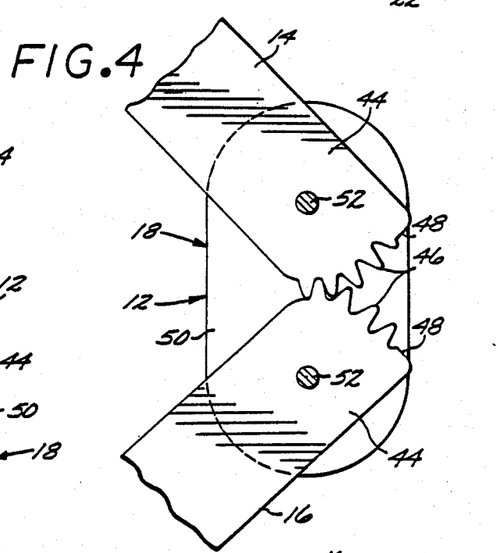
FIG. 4 is a sectional view, partly in elevation, similar to FIG. 3 but with the leaf springs pivoted to a flexion angle of slightly more than 90°.
Figure 5:
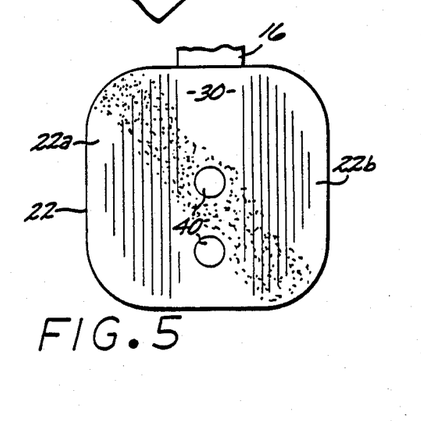
FIG. 5 is a plan view illustrating the cushioned inner surface of one of the load distribution pads.

Reference will now be made particularly to FIGS. 2, 3 and 4 which show the details of construction of the leaf spring hinge structure 12. Each of the leaf springs 14 and 16 includes a flat attachment end portion 38 rigidly attached to the respective pads 20 and 22, preferably by means of a plurality of fasteners 40 such as screws or rivets longitudinally spaced on the leaf spring attachment end portion 38. Moving toward the hinge 18, each of the leaf springs 14 and 16 next has a laterally outwardly bowed portion 42, and this bowed portion 42 terminates in a flat hinge portion 44. At the end of each flat hinge portion 44 is an arcuate array 46 of gear teeth which end in a stop shoulder 48 proximate the anterior edge of each leaf spring 14 and 16. The flat hinge portions 44 of leaf springs 14 and 16 are pivotally engaged between a pair of hinge plates 50 on respective pins 52 which may be rivets as shown. The gear teeth 46 on the hinged ends of leaf springs 14 and 16 are in meshing engagement which causes the springs 14 and 16 to pivot cooperatively and not independently relative to the hinge plates 50, and such cooperative pivoting of the springs 14 and 16 about the spaced axes of the pivot pins 52 causes the biaxial or bicentric hinge 18 to closely simulate the hinge action of the human knee. By this means, resistance of the hinge 28 to free pivoting or hinging movement of the knee is minimized. The leaf springs 14 and 16 and the hinge plates 50 are preferably made of aluminum for lightness in weight.

The double overlap or sandwich construction of the leaf springs 14 and 16 between the pair of hinge plates 50 is so stable in the transverse or lateral direction that the pivots can be quite free and do not need to be tight as in the single overlap pivot arrangements used in prior art devices intended for this same purpose of protection against injury from lateral forces, and such freedom of movement cooperates in minimizing resistance to knee movement, and hence in enabling full, free running movement to be achieved by an athlete wearing the device.

The leaf springs 14 and 16 are relatively long, and by having the upper leaf spring 14 attached to an upper portion of the thigh load distribution pad 20 and the lower leaf spring 16 attached to a lower portion of the shin load distribution pad 22, the regions of attachment of the springs 14 and 16 are, when the device 10 is worn, located respectively at a considerable distance above and below the actual knee joint adjacent to the strong bones of the leg, the femur and tibia, respectively. The stability of the double overlap, biaxial hinge 18, coupled with the long spring arms 14 and 16 attached to the pads 18 and 20, respectively, at considerable spacings from the knee joint, enable the device 10 to absorb forces and impacts directed toward the lateral side of the knee and distribute such forces and impacts in a cushioned manner at locations spaced substantially from the knee and in regions of strong bones of the leg. The generally rigid nature of the load distribution pads 20 and 22 causes such forces and impacts to be spread out over the substantial areas of the pads 20 and 22, and the spring action of the leaf springs 14 and 16 spreads the impact out not only in area, but also in time. The athletic knee protector 10 of the invention has the effect of distributing lateral forces generally over the whole leg as opposed to just on the point of the blow or closely adjacent to the knee, as with prior art devices which attempted to accomplish what the present invention in fact accomplishes.

The manner in which the leaf spring hinge structure 12 applies the load through the thigh and shin load distribution pads 20 and 22, respectively, at locations spaced substantially above and below the knee gains a series of advantages, all of which cooperate cumulatively or synergistically to afford protection to the knee joint that is of a different order of magnitude from any protection which could be provided by any prior art device or combination of prior art devices. First, the new structure of the present invention provides a long leaf spring for maximum deflectability and hence maximum capability of absorbing lateral forces and shocks. Second, there is a greatly increased lever arm relative to force application to the knee which decreases the force that the knee sees. The leverage is such that a large portion of the force is carried by the hip and ankle, with correspondingly reduced force being applied to the knee. Third, impacts are spread over time by the athletic knee protector of the present invention, greatly reducing the shock characteristics of impacts. Fourth, by applying forces and impacts through the thigh and shin pads at locations spaced substantially above and below the knee, the forces and impacts are applied to large muscle masses rather than substantially directly to bone as was the case with prior art devices, and these large muscle masses further absorb the forces and impacts by cushioning them and also spreading them out in time.

Figure 6:
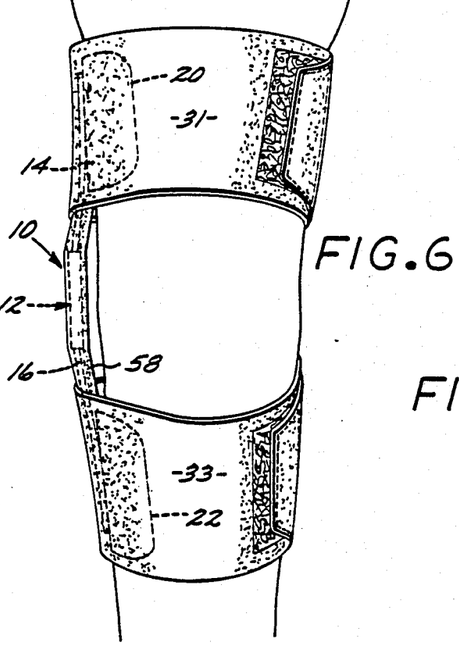
FIG. 6 is a fragmentary elevational view, with covered parts shown in dashed lines, showing the athletic knee protector of FIGS. 1-5 mounted on the leg of a wearer, with the knee and the athletic knee protector at approximately 60° of flexion.
Figure 7:
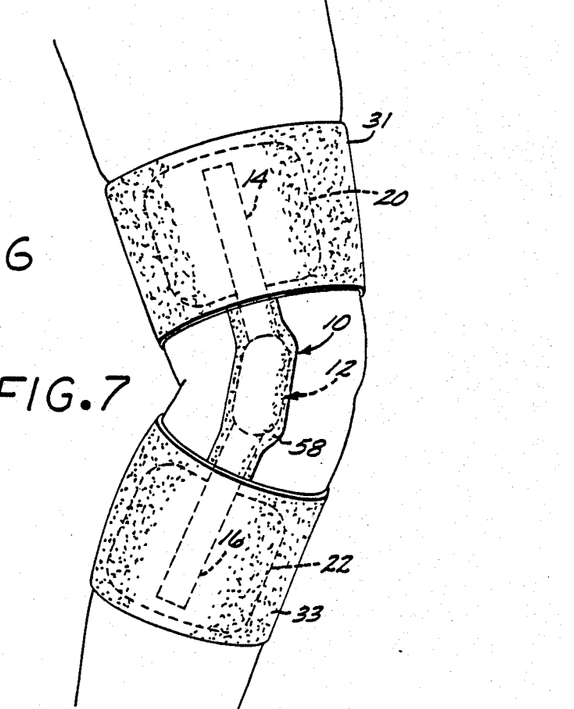
FIG. 7 is a view similar to FIG. 6, but with the knee and the athletic knee protector at approximately 30° of flexion.
Figure 8:
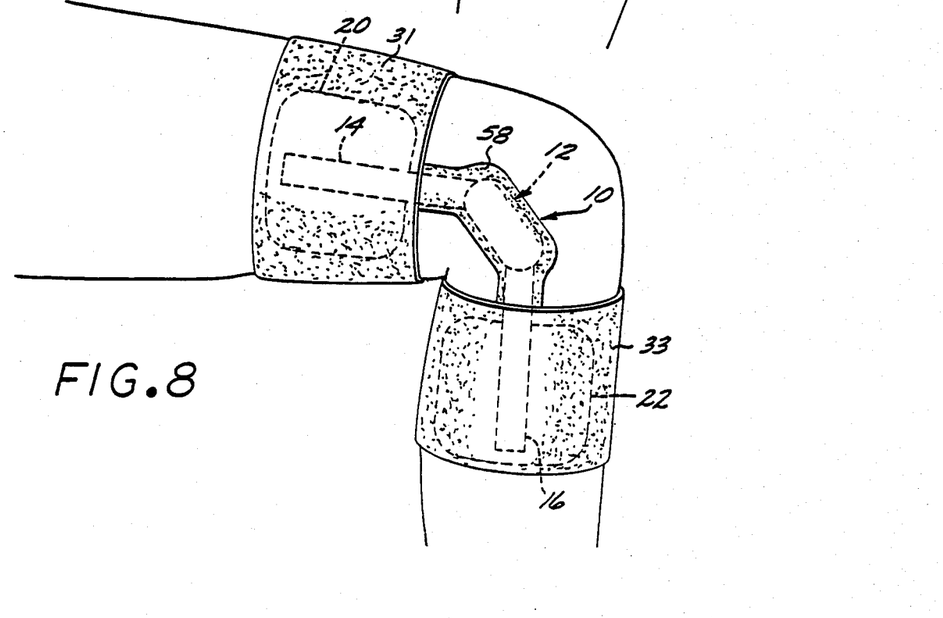
FIG. 8 is a view similar to FIGS. 6 and 7, but with the knee and the athletic knee protector at approximately 90° of flexion.
Figure 9:
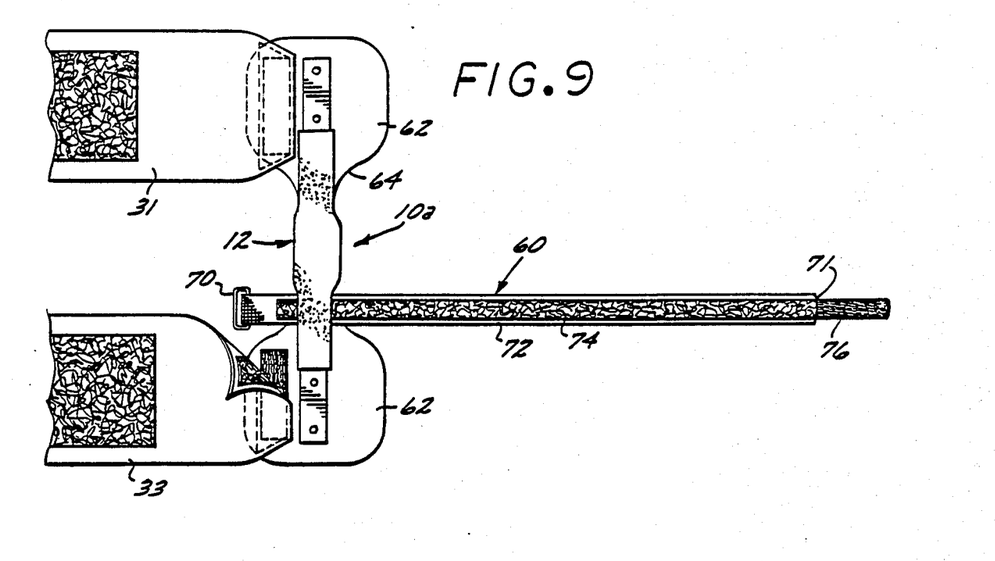
FIG. 9 is a fragmentary plan view similar to FIG. 1 of a fully assembled second form of athletic knee protector according to the invention which is modified to include an anti-migration strap, the athletic knee protector being laid out generally flat with the outer surfaces of the device facing upwardly.

In the form of the invention shown in FIGS. 1-8, the stop shoulders 48 come into engagement with each other as shown in FIG. 3 when the leaf springs 14 and 16 are extended slightly beyond axial alignment, which corresponds to a slight amount of extension of the knee. This prevents any further extension of the leaf springs 14 and 16, and thereby prevents any possibility of hyperextension of the knee. The hinge 18 allows pivoting from such slightly extended, stopped position through whatever angle of flexion may be necessary for any sport, as for example the slightly more than 90° of flexion illustrated in FIG. 4. FIGS. 6, 7 and 8 illustrate the athletic knee protector 10 of the invention operatively located, with the knee in three different conditions of flexion. FIG. 6 illustrates the knee protector 10 with the knee at approximately 0° of flexion, or possibly slightly extended with the device substantially in the hinged condition of FIG. 3; FIG. 7 illustrates the knee protector 10 with the knee, and hence also the leaf spring hinge structure 12, at approximately 30° of flexion; and FIG. 8 illustrates the knee, and hence the leaf spring hinge structure 12, at approximately 90° of flexion.

It will be seen in FIGS. 6, 7 and 8 that the hinge 18 and flat hinge portions 44 and outwardly bowed portions 42 of leaf springs 14 and 16 are covered by a foam elastomer sleeve or sheath 58. Sleeve 58 may be installed prior to attachment of at least one of the leaf spring end portions 38 to its respective load distribution pad 20 and 22, or may alternatively be folded over leaf springs 14 and 16 and hinge 18 and stitched together along one edge. This foam elastomer sleeve 58 may be made of foam neoprene, and serves the dual functions of protecting another person from being injured who may impact the hinge structure 12, and also cooperates with the leaf springs 14 and 16 in extending the time of application of any impact to the load distribution pads 20 and 22 and hence to the thigh and shin. If desired, additional foam underpadding may cover the hinge 18 underneath the sleeve 58 as a further protective measure.

As best seen in FIGS. 2 and 6, there is substantial lateral spacing between the hinge 18 and the outwardly bowed portions 42 of both of the leaf springs 14 and 16 on the one hand and the load distribution pads 20 and 22 on the other hand. This is essential for effective operation of the athletic knee protector 10 in protecting the knee of the wearer from lateral forces and impacts, as the filling of this void with any material, even a foam plastic material, would enable at least part of any lateral force or impact to be transmitted directly to the knee and would correspondingly diminish the effectiveness of the knee protector 10. With the complete void in this region, the knee protector 10 of the invention is enabled to substantially completely protect the knee from lateral forces or impacts.

Since the athletic knee protector 10 of the invention requires the leaf spring hinge structure 12 on only the lateral side thereof and requires no hinge structure on the medial side of the device, this leaves the medial side substantially unobstructed for freedom in athletic movement.

Figure 10:
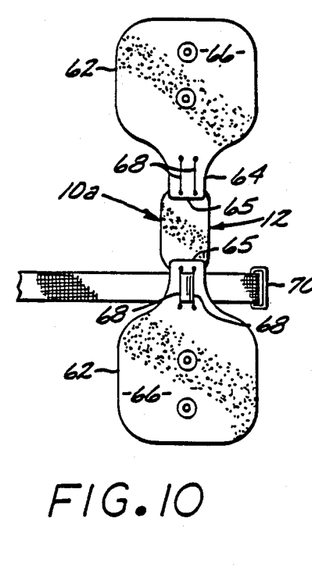
FIG. 10 is a fragmentary plan view of the device shown in FIG. 9 with the elastomer attachment sheets removed, the device being laid out flat with the inner surfaces of the device facing upwardly.
Figures 11, 12:
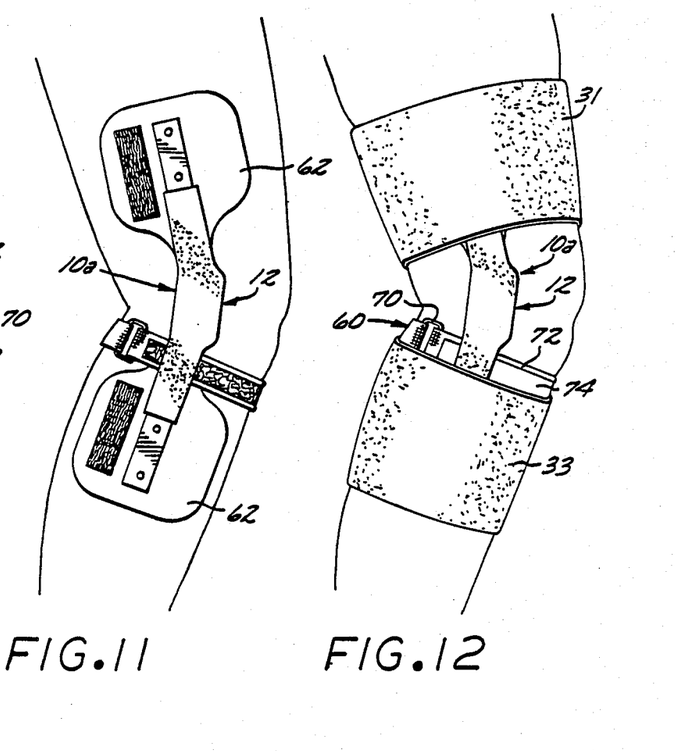
FIG. 11 is a side elevational view illustrating the athletic knee protector of FIGS. 9 and 10 operatively positioned on the leg of a wearer with the anti-migration strap engaged about the calf, the device being illustrated without the elastomer attachment sheets which secure the load distribution pads to the thigh and shin.
FIG. 12 is a view similar to FIG. 11, but with the thigh and shin load distribution pads attached to the thigh and shin by means of the elongated elastomer attachment sheets.
Figures 13, 14, 15, 16, 17:
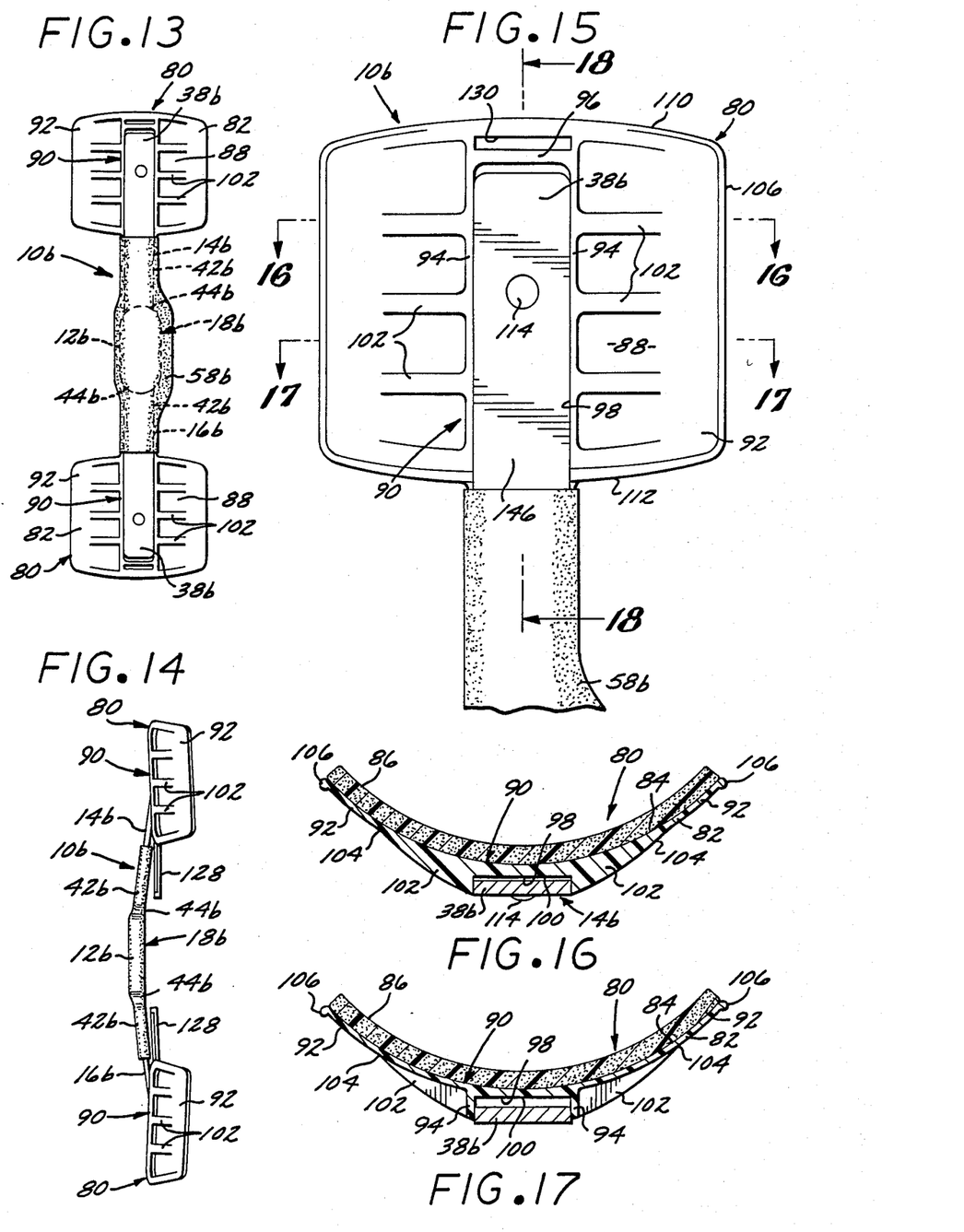
FIG. 13 is a lateral side elevational view of a third and presently preferred form of the invention shown without the elastomer attachment sheets and Velcro connections therefor, wherein the load distribution pads or cuffs are each pivotal or rockable in the general lateral/medial direction for self-adjustment to the contours of the leg to eliminate preloading of the knee joint, and wherein the load distribution pads or cuffs also have a variable flexibility in the anterior/posterior direction for improved adaptation of the pads or cuffs to the curvature of the leg.
FIG. 14 is a front elevational view of the form of the invention shown in FIG. 13.
FIG. 15 is an enlarged, fragmentary side elevational view showing a portion of the device shown in FIGS. 13 and 14.
FIG. 16 is a transverse sectional view taken on the line 16—16 in FIG. 15.
FIG. 17 is a transverse sectional view taken on the line 17—17 in FIG. 15.
Figure 18:
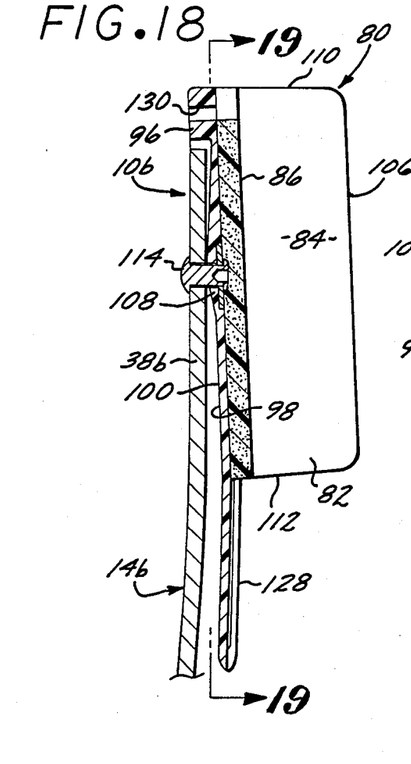
FIG. 18 is a fragmentary longitudinal sectional view taken on the line 18—18 in FIG. 15.
Figure 19:
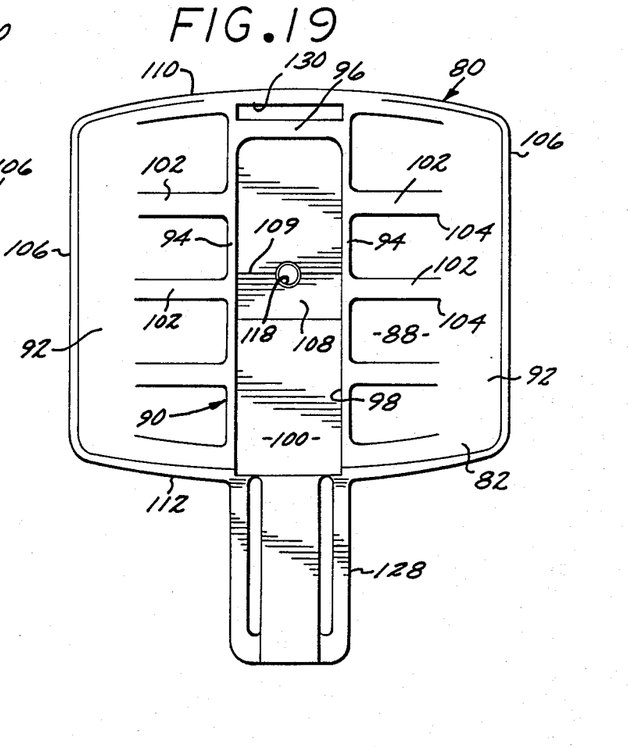
FIG. 19 is a longitudinal sectional view taken on the line 19—19 in FIG. 18, showing the lateral or outer side of one of the load distribution pads or cuffs.
Figure 20:
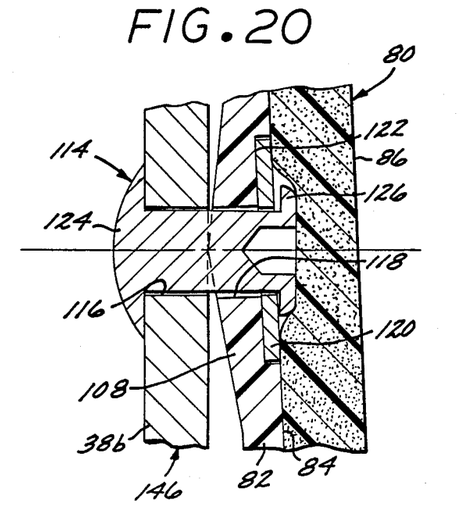
FIG. 20 is a greatly enlarged fragmentary longitudinal sectional view further illustrating the pivotal region of FIG. 18.
Figure 21:
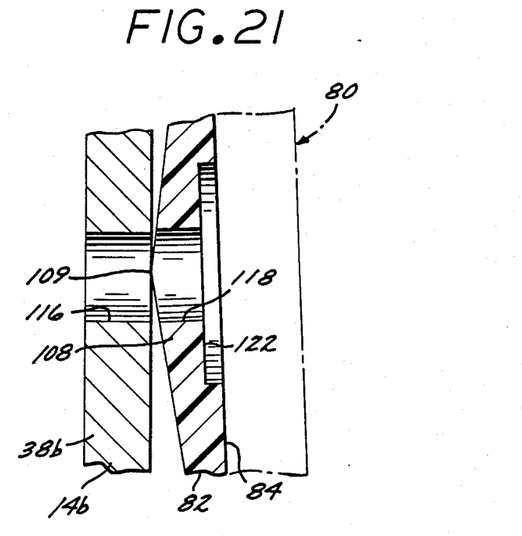
FIG. 21 is a view similar to FIG. 20, but with the rivet and washer of the pivotal connection removed.

FIGS. 9-12 illustrate a second form of athletic knee protector according to the invention, this form being generally designated 10a. The athletic knee protector 10a of FIGS. 9-12 is identical to the athletic knee protector 10 of FIGS. 1-8 except for the addition of an anti-migration strap 60 and modified load distribution pads 62 which each have an integral tongue 64 extending in the general longitudinal direction of the knee protector 10a in the proximal direction toward the knee as best seen in FIG. 10. With the athletic knee protector 10a mounted on a leg of a user, the proximal inner, free ends 65 of tongues 64 extend close to but just short of the actual knee joint. Foam elastomer linings 66 cover the inner surfaces of the load distribution pads 62, the foam elastomer linings 66 being coextensive with the respective load distribution pads so as to cover not only the wide portions of the pads 62 but also the tongues 64.

A pair of longitudinally arranged, parallel strap slots 68 extends through each of the tongues 64, including the foam lining portions 66. By thus having a strap tongue 64 with strap-receiving slots 68 on each of the load distribution pads 62, the athletic knee protector 10a is adapted for operative mounting on the lateral side of either leg, with the anti-migration strap 60 engaged through the strap slots 68 of the tongue 64 which is below the hinge structure 12 for that particular leg. The athletic knee protector 10a as illustrated in FIGS. 9-12 is adapted for use on the lateral side of the right leg. The same athletic knee protector 10a is adaptable for mounting on the lateral side of the left leg by simply inverting the knee protector 10a so that the hinge structure 12 is in the proper direction for flexion with the leg, and when thus inverted for use on the left leg, the anti-migration strap 60 must be moved from the location illustrated in FIGS. 9-12 and engaged through the strap slots 68 of the other tongue 64.

The anti-migration strap 60 is made of a material that is flexible but substantially nonstretchable, as for example a heavy woven nylon belt-type material. A rigid loop 70, preferably of metal, is secured to one end of strap 60 and is adapted to have the other free end 71 of strap 60 engaged therethrough. The outer surface 72 of strap 60 has a Velcro pad strip 74 extending along most of its length, and an outwardly facing Velcro hook strip 76 extends longitudinally from the free end 71 of strap 60. When the strap 60 is engaged around the upper calf of the wearer, the Velcro hook strip 76 and free end 71 of strap 60 are engaged through the strap loop 70 and doubled back over the outside of strap 60, the Velcro hook strip 76 then being attached to the outwardly exposed Velcro pad strip 74 with the strap snugly secured about the calf where the calf flares outwardly immediately below the knee joint. This provides a positive interlock between the anti-migration strap 60 and the flare of the calf which prevents any downward migration of the athletic knee protector 10a on the leg, and retains the hinge structure 12 substantially in registry with the knee joint despite heavy athletic use, and even despite any tendency the knee protector might otherwise have to slip because of the presence of perspiration between the foam elastomer linings 66 and the leg.

It is to be noted that the anti-migration strap 60 is attached to a tongue 64 of one of the load distribution pads 62 rather than being attached to or engaged over the leaf-spring hinge structure 12. This avoids any tendency to compress the leaf-spring hinge structure 12 toward the knee joint, leaving the hinge structure 12 spaced outwardly from the knee as seen in FIG. 6 so as to be effective in absorbing lateral forces and impacts without transmitting them directly to the knee.

FIGS. 13-21 illustrate a third form of athletic knee protector according to the invention which embodies two new features not found in the forms of the invention shown in FIGS. 1-8 and 9-12. While these two new features find particular utility in connection with the athletic knee protector of the invention which protects the knee of either leg against injury from lateral forces and impacts, these new features are also useful when embodied in any protective or prophylactic knee brace which has thigh and shin cuffs connected to respective bars which are hingedly connected proximate the knee by hinge means which provides a substantially rigid connection between the bars in the lateral/medial direction.

One of these new features of the third form of the invention shown in FIGS. 13-21 is a floating, rocking, or tilting action of each of the cuffs or load distribution pads relative to its respective bar or leaf spring member about an axis which is transverse to the longitudinal direction of the respective bar or leaf spring member, and directed in the general anterior/posterior direction. This floating, rocking, or tilting action of the cuffs or load distribution pads relative to their respective hinged bars or leaf spring members allows the cuffs or load distribution pads to self-adjust to the lateral or outer contours of the leg so as to substantially completely eliminate any tendency for the prophylactic knee brace or athletic knee protector to preload ligaments of the knee at any condition of flexion of the knee, or during working of the knee as during walking or running. This floating or rocking action also helps assure substantially uniform distribution of lateral forces and impacts over the areas of the cuffs or load distribution pads as the forces and impacts are applied to the thigh and shin.

The second new feature of the form of the invention illustrated in FIGS. 13-21 is a variable rigidity of the cuffs or load distribution pads from a generally rigid central structure of each cuff or load distribution pad proximate its connection to its respective hinged bar or leaf spring member to a gradually increasing flexibility in the anterior/posterior direction outwardly toward anterior/posterior edge portions of each cuff or load distribution pad which are somewhat flexible. This variation from generally rigid centrally to somewhat flexible anterior/posterior portions provides improved adaptation of the cuffs or pads to the curvature of the leg for more secure attachment to the leg. It may also be coupled with a concavity of the cuffs or load distribution pads which has a somewhat smaller or tighter generally cylindrical radius of curvature than the curvatures of the lateral side of the leg against which the cuffs or load distribution pads are secured, which causes the sides of the cuffs or load ditribution pads to flex laterally outwardly in their attached positions against the leg and thereby attach ever more securely to the leg and distribute lateral forces and impacts more uniformly over the entire areas of the cuffs or load distribution pads.

Referring to FIGS. 13-21, the third form 10b of athletic knee protector of the invention has as its principal structural basis leaf spring hinge structure 12b which includes a pair of leaf spring members 14b and 16b that correspond in configuration to the leaf spring members 14 and 16 of FIGS. 1-8. Leaf spring members 14b and 16b each have a flat attachment end portion 38b to which the cuffs or load distribution pads are attached, an outwardly bowed portion 42b, and a flat hinge portion 44b. The hinge portions 44b of leaf spring members 14b and 16b are hingedly connected by means of biaxial or bicentric hinge structure 18b generally corresponding in configuration to hinge structure 18 of FIGS. 1-8 which provides substantially free anterior/posterior pivotal movement between the leaf spring members 14b and 16b corresponding to anterior/posterior pivotal movement of the knee, but provides a substantially rigid connection between the leaf spring members 14b and 16b in the lateral/medial direction. The leaf spring hinge structure 12b in the form of the invention illustrated in FIGS. 13-21 is the same as leaf spring hinge structure 12 shown in FIGS. 1-8, with the exception that the stop shoulders corresponding to shoulders 48 shown in FIGS. 3 and 4 are arranged to stop the leaf spring members 14b and 16b slightly on the flexion side of axial alignment so as to assure against any possible extension of the knee during athletic endeavor.

The two load distribution pads of the third form of the invention shown in FIGS. 13-21 are each generally designated 80, and preferably each have the same construction and configuration. Becase of the somewhat smaller or tighter generally cylindrical radius of curvature of the pads 80, they have more the appearance of cuffs than the load distribution pads 20 and 22 of the first form of the invention shown in FIGS. 1–8 and load distribution pads 62 of the second form of the invention shown in FIGS. 9–12. Hence, the load distribution pads 80 of the third form of the invention shown in FIGS. 13–21 will be referred to hereinafter as cuffs.

Each of the cuffs 80 is considerably modified in construction relative to the load distribution pads of the first and second forms of the invention. Thus, each of the cuffs 80 has a shell 82 which defines its overall plan form, and which is shaped generally as a section of a right circular cylinder. The medial or inner side 84 of each cuff shell 82 has a generally cylindrical surface covered by a foam elastomer sheet 86 which is the functional counterpart of the foam elastomer sheets 28 and 30 of the first form of the invention shown in FIGS. 1–8. The lateral or outer side of shell 82 is generally designated 88, and it is provided with a laterally outwardly projecting rib structure which forms a generally rigid central structure 90 of each cuff 80 (central in the anterior/posterior direction) proximate the connection of the cuff 80 to the respective leaf spring member 14b or 16b, with the cuff rigidity gradually tapering off in the anterior/posterior direction, and the rib structure terminating anteriorly and posteriorly at locations spaced inwardly or centrally from the anterior and posterior edges of each cuff shell 82 so as to leave anterior and posterior sections 92 of shell 82 which are unstiffened and have a measure of flexibility.

The plastic material of which each cuff 80 is made is a material which is generally rigid structurally when relatively thick, but is resiliently flexible when made relatively thin. A large number of plastic materials have such physical characteristics, and a suitable material can be readily selected by those having ordinary skill in the art. One example of such a material is high density polyethylene.

The substantially rigid central structure 90 of each cuff 80 is provided with a portion of its rigidity in the longitudinal direction of leaf spring members 14b and 16b by means of a pair of spaced, parallel longitudinal ribs 94 extending laterally outwardly from shell 82, and a transverse rib 96 extending laterally outwardly from shell 82 and merging into the distal end portions of the longitudinal ribs 94 (distal relative to the knee). Longitudinal ribs 94 and transverse rib 96 define a laterally outwardly facing longitudinal recess 98 having a bottom 100 in each cuff 80.

The rigidity of substantially rigid central structure 90 is contributed to by central portions of two spaced-apart sets of transverse, generally parallel, tapered stiffening ribs 102, one set on the anterior/posterior side of one longitudinal rib 94 which merges with that longitudinal rib 94, and the other set on the anterior/posterior side of the other longitudinal rib 94 which merges with such longitudinal rib 94. Each set of transverse stiffening ribs 102 joins into its respective longitudinal rib 94, having substantially the same lateral height as the respective longitudinal rib 94 at the merger or juncture, and then continuously decreases in lateral height in the anterior/posterior direction, tapering down to anterior/posterior ends which fair or feather into the shell 82 intermediate the respective longitudinal ribs 94 and respective anterior/posterior edge 104 of shell 82. This leaves the unribbed, unstiffened anterior/posterior sections 92 of shell 82 with some flexibility.

A transverse fulcrum rib or projection 108 having an apex 109 extends between the longitudinal ribs 94 of each cuff 80, projecting upwardly from the bottom 100 of longitudinal recess 98. This fulcrum rib 108 is a shallow rib which is preferably generally triangular in cross-section, but may alternatively be somewhat rounded proximate its apex 109. The apex 109 of fulcrum rib 108 is preferably closer to the distal edge 110 of cuff 80 than to its proximal edge 112 to emphasize the distance from the knee at which lateral forces and impacts transmitted to the cuffs 80 through the fulcrum ribs 108 are averaged over the cuff 80 when applied to the thigh and shin of the wearer. The flat attachment end portion 38b of each leaf spring member 14b and 16b is engaged in the longitudinal recess 98 of a respective cuff 80 so that its medial side rests against the respective fulcrum rib 108.

The respective cuff 80 is riveted to the respective leaf spring member 14b or 16b by means of a rivet 114 which extends through a rivet hole 116 through the respective leaf spring member 14b or 16b and through an aligned rivet hole 118 through the respective cuff 80, rivet hole 118 extending through the apex region of the respective fulcrum rib 108. A washer 120 is seated in an enlarged annular recess 122 in the medial side of cuff 80, and the rivet 114 has a head 124 on the lateral side of the respecctive leaf spring member 14b or 16b and an upset end 126 on the medial side of the washer 120. Annular clearance is provided between the shank of rivet 114 and one or both of the rivet holes 116 and 118, and the spacing between rivet head 124 and upset end 126 is slightly greater than the combined lengths of rivet holes 116 and 118 and thickness of washer 120, so as to allow the cuff 80 to freely tilt or rock in a floating manner about the fulcrum rib 108. This rocking action is thus in the general lateral/medial direction about an axis which is in the anterior/posterior direction and is transverse to the longitudinal axis of the respective leaf spring member 14b or 16b. When the cuffs 80 are rocked about this axis of the fulcrum ribs 108, they appear to have a teeter-totter or wiggle-waggle type of action.

This free floating or rocking action of the cuffs 80 relative to their respective leaf spring members 14b and 16b enables one of the cuffs 80 to self-adjust for accommodation to the lateral contour of the thigh, and the other cuff 80 to self-adjust for accommodation to the lateral contour of the calf. These lateral contours of the thigh and calf will vary according to the angle of flexion of the knee, and according to variations in the tension of the muscles in the thigh and calf, and the free floating, rocking action of the cuffs 80 will accommodate any such variations as the wearer flexes the knee during physical activity such as walking or running. By this means, the athletic knee protector 10b of FIGS. 13–21 substantially completely avoids preloading of the knee at any angle of flexion of the knee, and consequently avoids the usual predisposition of the knee to injury when it is preloaded as it would be with prior art athletic knee protectors and prophylactic knee braces.

The relatively thin shell 82 of each cuff 80, coupled with the substantially rigid central structure 90 and two series or sets of tapered transverse stiffening ribs 102 which progressively decrease in height in the anterior/posterior direction, fairing into the shell 82 short of the anterior/posterior edges 106 so as to leave unribbed, unstiffened anterior/posterior sections 92 of shell 82, provide a gradually and continuously increasing flexibility of the cuffs 80 in the anterior/posterior direction which enables the cuffs 80 to adapt to the anterior/posterior contours or curvatures of the thigh and shin in such a way as to generally equalize the application of the forces involved in attachment of the cuffs 80 to the thigh and shin, and also to generally equalize the application of externally applied lateral forces and impacts over the areas of the medial sides of the cuffs in the anterior/posterior direction. The variation from generally rigid centrally to somewhat flexible anterior/posterior portions of the cuffs 80 is preferably coupled with a concavity of each of the cuffs which is made with a somewhat smaller or tighter generally cylindrical radius of curvature than the opposing curvatures of the lateral side of the leg against which the cuffs are secured. This causes the anterior/posterior portions of the cuffs 80 to flex in their attached positions against the thigh and calf, and causes distribution of lateral forces and impacts to be more uniformly applied over the areas of the cuffs across the anterior/posterior extent of the cuffs.

Thus, while the floating, rocking action of the cuffs avoids preloading and causes distribution of lateral forces and impacts more uniformly over the areas of the cuffs in the longitudinal direction (relative to leaf spring members 14b and 16b), the variable flexibility of the cuffs in the anterior/posterior direction coupled with the tighter radius of curvature of the cuffs than the registering curvatures of the leg causes distribution of lateral forces and impacts more uniformly over the areas of the cuffs across the anterior/posterior direction, whereby the overall distribution of lateral forces and impacts as applied by the cuffs 80 to the thigh and calf of the wearer are generally uniform and are much more uniform than for prior art athletic knee protector devices.

As with the other two forms of the invention, the athletic knee protector 10b of FIGS. 13-21 may be attached to the leg of the wearer by means of Velcro-fastened elastomer attachment sheets such as the attachment sheets 31 and 33 of the other forms, or may alternatively be attached by taping the cuffs or load distribution pads 80 into position on the thigh and calf.

If desired, a slotted tongue 128 may be provided on each of the cuffs 80 extending proximally from the proximal edge 112 of the cuff 80 for use of an anti-migration strap such as the anti-migration strap 60 shown in FIGS. 9-12 and described in detail hereinabove. As an alternative anti-migrations means, a transverse slot 130 is provided through the transverse rib 96 of each cuff 80 proximate the distal edge 110 of cuff 80, through which a suspension strap (not shown) may be engaged for connecting the upper end of athletic knee protector 10b to the belt or a fastening device on the clothing of the wearer. The foam elastomer sheet 86 is cut away in the region of transverse slot 130.

A protective foam elastomer sleeve or sheath 58b is engaged over the hinge structure 18b and bowed portions 42b of leaf spring members 14b and 16b. The ends of sleeve 58b are preferably short of the proximal edges 112 of cuffs 80 so as to not interfere with the rocking action of the cuffs.

In the appended claims, the term "knee protection device" is intended to refer not only to an athletic knee protector but also to other types of hinged knee braces. Also, in the claims, the terms "bar means" is intended to refer not only to leaf spring members for athletic knee protectors of the character shown and described in detail herein, but also to brace bars embodied in other types of hinged knee braces.

While the instant invention has been described with regard to particular embodiments, modifications may readily be made by those skilled in the art, and it is intended that the claims cover any such modifications which fall within the spirit and scope of the invention.

We claim:

1. A knee protection device which comprises:
    elongated thigh bar means having a lower portion located generally laterally of the knee and extending upwardly to an upper portion spaced substantially above the knee;
    elongated shin bar means having an upper portion located generally laterally of the knee and extending downwardly to a lower portion spaced substantially below the knee;
    hinge means hingedly connecting said lower portion of said thigh bar means and said upper portion of said shin bar means, said hinge means providing substantially free anterior/posterior pivotal movement between said thigh and shin bar means corresponding to anterior/posterior pivotal movement of the knee, but providing a substantially rigid connection between said thigh and shin bar means in the lateral/medial direction; and
    thigh pad means having a lateral side pivotally connected to said upper portion of said thigh bar means for rocking movement in the general lateral/medial direction, and shin pad means having lateral side pivotally connected to said lower portion of said shin bar means for rocking movement in the general lateral/medial direction;
    said pivotal connections each including fulcrum rib means on the lateral side of the respective pad means, said fulcrum rib means having a fulcrum apex which rockingly engages against the respective said bar means;
    said thigh pad means being attachable to the lateral side of the thigh of the wearer, and said shin pad means being attachable to the lateral side of the shin of the wearer;
    said rocking movement of said thigh pad means relative to said thigh bar means and of said shin pad means relative to said shin bar means enabling said thigh and shin pad means to follow the lateral contours of the leg when they are attached to the thigh and shin, respectively, thereby avoiding preloading of the knee by said knee protection device.

2. A knee protection device as defined in claim 1, wherein said thigh bar means comprises a thigh leaf spring and said shin bar means comprises a shin leaf spring;
    said leaf springs and said hinge means together defining a bowed leaf spring structure that is generally continuously bowed between said upper portion of said thigh bar means and said lower portion of said shin bar means, said leaf springs bowing laterally outwardly from said upper portion of said thigh bar means and said lower portion of said shin means so that said hinge means is substantially spaced laterally outwardly from the knee of the wearer; and
    said bowed leaf spring structure being resiliently flexible in the lateral/medial direction so as to absorb forces and impacts directed toward the lateral side of the knee, distributing such forces and impacts in a cushioned manner through said thigh and shin pad means to the thigh and shin, respectively, at locations substantially spaced from the knee.

3. A knee protection device as defined in claim 1, wherein said thigh pad means has a lower edge relatively proximal to the knee and an upper edge relatively distal to the knee, and said shin pad means has an upper edge relatively proximal to the knee and a lower edge relatively distal to the knee, and wherein each of said pivotal connections is closer to the said distal edge of the respective said pad means than to the said proximal edge.

4. A knee protection device as defined in claim 1, wherein at least one of said pad means comprises cuff means having anterior/posterior portions, and a generally cylindrically contoured medial side adapted to engage against the lateral side of the leg;

said cuff means including means to provide a variable rigidity of said cuff means in the anterior/posterior direction, said cuff means having its maximum rigidity proximate to its said pivotal connection to the respective said bar means, and decreasing in rigidity toward anterior/posterior portions spaced from the respective said bar means to provide some flexibility in the lateral/medial direction for adaptation of said cuff means to the curvature of the leg.

5. A knee protection device as defined in claim 4, wherein each of said pad means comprises a said cuff means, said thigh pad means being thigh cuff means and said shin pad means being shin cuff means.

6. A knee protection device as defined in claim 4, wherein the generally cylindrically contoured medial side of said cuff means is formed with a contour having a smaller radius of curvature than the curvature of the leg against which it is adapted to be engaged, whereby said anterior/posterior portions of said cuff means are adapted to flex laterally outwardly when said cuff means is compressed against the leg.

7. A knee protection device as defined in claim 6, wherein each of said pad means comprises a said cuff means.

8. A knee protection device as defined in claim 5, wherein said variable rigidity is provided by tapered rib means on the lateral side of each of said cuff means.

9. A knee protection device as defined in claim 5, wherein said thigh bar means comprises a thigh leaf spring and said shin bar means comprises a shin leaf spring;

said leaf springs and said hinge means together defining a bowed leaf spring structure that is generally continuously bowed between said upper portion of said thigh bar means and said lower portion of said shin bar means; said leaf springs bowing laterally outwardly from said upper portion of said thigh bar means and said lower portion of said shin bar means so that said hinge means is substantially spaced laterally outwardly from the knee of the wearer; and said bowed leaf spring structure being resiliently flexible in the lateral/medial direction so as to absorb forces and impacts directed toward the lateral side of the knee, distributing such forces and impacts in a cushioned manner through said thigh and shin cufff means to the thigh and shin, respectively, at locations substantially spaced from the knee.

10. A knee protection device which comprises:
elongated thigh bar means having a lower portion located generally laterally of the knee and extending upwardly to an upper portion spaced substantially above the knee;

elongated shin bar means having an upper portion located generally laterally of the knee and extending downwardly to a lower portion spaced substantially below the knee;

hinge means hingedly connecting said lower portion of said thigh bar means and said upper portion of said shin bar means, said hinge means providing substantially free anterior/posterior pivotal movement between said thigh and shin bar means corresponding to anterior/posterior pivotal movement of the knee; and thigh pad means having a lateral side connected to said upper portion of said thigh bar means and being attachable to the lateral side of the thigh of the wearer, and shin pad means having a lateral side connected to said lower portion of said shin bar means and being attachable to the lateral side of the shin of the wearer;

at least one of said pad means comprising cuff means having anterior/posterior portions, and a generally cylindrically contoured medial side adapted to engage against the lateral side of the leg, said cuff means including means to provide a variable rigidity of said cuff means in the anterior/posterior direction, said cuff means having its maximum rigidity centrally proximate to its connection to the respective said bar means, and decreasing in rigidity to toward anterior/posterior portions spaced from the respective said bar means to provide some flexibility in the lateral/medial direction for adaptation of said cuff means to the curvature of the leg.

11. A knee protection device as defined in claim 10, wherein each of said pad means comprises a said cuff means, said thigh pad means being thigh cuff means and said shin pad means being shin cuff means.

12. A knee protection device as defined in claim 10, wherein the generally cylindrically contoured medical side of said cuff means is formed with a contour having a smaller radius of curvature than the curvature of the leg against which it is adapted to be engaged, whereby said anterior/posterior portions of said cuff means are adapted to flex laterally outwardly when said cuff means is compressed against the leg.

13. A knee protection device as defined in claim 12, wherein each of said pad means comprises a said cuff means.

14. A knee protection device as defined in claim 11, wherein said variable rigidity is provided by tapered rib means on the lateral side of each of said cuff means.

15. A knee protection device as defined in claim 11, wherein said thigh bar means comprises a thigh leaf spring and said shin bar means comprises a shin leaf spring;

said leaf springs and said hinge means together defining a bowed leaf spring structure that is generally continuously bowed between said upper portion of said thigh bar means and said lower portion of said shin bar means; said leaf springs bowing laterally outwardly from said upper portion of said thigh bar means and said lower portion of said shin bar means so that said hinge means is substantially spaced laterally outwardly from the knee of the wearer; and said bowed leaf spring structure being resiliently flexible in the lateral/medial direction so as to absorb forces and impacts directed toward the lateral side of the knee, distributing such forces and impacts in a cushioned manner through said thigh and shin cuff means to the thigh and shin, respectively, at locations substantially spaced from the knee.

* * * * *